(12) United States Patent
De Nando et al.

(10) Patent No.: US 9,237,928 B2
(45) Date of Patent: Jan. 19, 2016

(54) MOBILE FUNCTIONAL HOSPITAL UNIT FOR THE TEMPORARY DISTRIBUTION OF MEDICAL FLUIDS

(75) Inventors: Vittorio De Nando, Settimo Milanese (IT); Patrick Deneux, Milan (IT); Nathalie Demerville, Bovisio Masciago (IT)

(73) Assignee: Air Liquide Sanita Service SpA, Milan (IT)

( * ) Notice: Subject to any disclaimer, the term of this patent is extended or adjusted under 35 U.S.C. 154(b) by 2145 days.

(21) Appl. No.: 12/062,701

(22) Filed: Apr. 4, 2008

(65) Prior Publication Data

US 2009/0121592 A1    May 14, 2009

(30) Foreign Application Priority Data

Apr. 6, 2007 (EP) ..................................... 07300937

(51) Int. Cl.
*A61M 16/01* (2006.01)
*A61B 19/02* (2006.01)
(Continued)

(52) U.S. Cl.
CPC ............ *A61B 19/0248* (2013.01); *A61M 16/01* (2013.01); *A61M 16/10* (2013.01); *A61B 2017/00119* (2013.01); *A61B 2017/00199* (2013.01); *A61M 2202/025* (2013.01); *A61M 2202/0208* (2013.01); *A61M 2202/0283* (2013.01); *A61M 2205/502* (2013.01); *A61M 2205/583* (2013.01); *A61M 2209/084* (2013.01)

(58) Field of Classification Search
CPC ................ A61M 16/01; A61M 16/10; A61M 2205/502; A61M 2209/084
USPC ...................................... 137/899, 899.4, 377; 128/200.24–207.18; 312/249.8; 248/647; 280/79.6
See application file for complete search history.

(56) References Cited

U.S. PATENT DOCUMENTS

| 3,428,383 | A |   | 2/1969 | Nobel |
| 4,020,834 | A | * | 5/1977 | Bird .......................... 128/204.25 |
| 5,307,839 | A | * | 5/1994 | Loebker et al. ................ 137/899 |

(Continued)

FOREIGN PATENT DOCUMENTS

| EP |   0 464 410 A2 | 1/1992 |
| WO | WO 2004/084981 | 10/2004 |
| WO | WO 2006/074473 | 7/2006 |

OTHER PUBLICATIONS

Sfar: "Une Aide a la Lecture pour l'Arrete du Oct. 3, 1995 Relatif aux Modalites de-Utilisation et de Controle des Materiels et Dispositifs Medicaux" Internet Article, 1996.

(Continued)

*Primary Examiner* — Kevin Murphy
(74) *Attorney, Agent, or Firm* — Allen E. White (57) ABSTRACT

Mobile functional hospital unit (1) for the temporary distribution of medical fluids, comprising at least one rear outlet (5, 25; 30) for tapping off medical fluid designed and able to be connected to a medical fluid distribution network arranged within a hospital building and associated with the rear wall (6) of the cabinet (2), at least one side outlet (21, 22, 23, 24; 17) for tapping off medical fluid associated with at least one side wall (27, 28) of the cabinet (2), and at least one connecting line (9) fluidically connecting at least one gas cylinder (3, 4; 7, 8) to at least one of the rear (5, 25) and side (21, 22, 23, 24) gas tapping outlets in order to supply at least one of the rear (5, 25) and side (21, 22, 23, 24) outlets with gas delivered by at least one gas cylinder (3, 4; 7, 8).

28 Claims, 5 Drawing Sheets

(51) Int. Cl.
*A61M 16/10* (2006.01)
*A61B 17/00* (2006.01)

(56) References Cited

U.S. PATENT DOCUMENTS

| | | | |
|---|---|---|---|
| 5,337,845 A | 8/1994 | Foster et al. | |
| 5,497,766 A * | 3/1996 | Foster et al. | 128/200.24 |
| 5,570,895 A * | 11/1996 | McCue et al. | 280/47.19 |
| 5,899,469 A * | 5/1999 | Pinto et al. | 280/79.11 |
| 5,966,760 A * | 10/1999 | Gallant et al. | 5/658 |
| 6,217,328 B1 * | 4/2001 | Oliver | 433/80 |
| 6,669,224 B2 * | 12/2003 | Newkirk | 280/508 |
| 6,733,017 B2 * | 5/2004 | Intravatola | 280/79.6 |
| 2004/0168686 A1* | 9/2004 | Krebs | 128/203.12 |
| 2006/0170314 A1* | 8/2006 | Ricker et al. | 312/290 |

OTHER PUBLICATIONS

Taema: "Anaesthesia Tray Clarys 2000" Internet Article, Nov. 6, 2001; URL:http://www.taema.com/en/business/hopital/clarys2000_%20%20GB.pdf.

Taema: "Anaesthesia Tray Felix Visio", Internet Article, Apr. 29, 2004, URL:http://www.taema.com/en/business/hopital/felixvisio.pdf.

Draeger: "Anesthesia tray Zeus", Internet Article, Nov. 13, 2006; URL:http://www.draeger.com/MT/internet/pdf/lib/de/anesth_work/Zeus_br.pdf.

European Search Report dated Oct. 29, 2007.

* cited by examiner

MOBILE FUNCTIONAL HOSPITAL UNIT FOR THE TEMPORARY DISTRIBUTION OF MEDICAL FLUIDS

CROSS REFERENCE TO RELATED APPLICATIONS

The present application claims the benefit of priority under 35 U.S.C. §119 (a) and (b) to European patent application No. 07300937.5, filed Apr. 6, 2007, the entire contents of which are incorporated herein by reference.

BACKGROUND

1. Field of the Invention

The present invention relates to a functional unit for temporarily distributing fluids, that is to say gas and vacuum and auxiliary services in a hospital environment. In particular, the present invention relates to a backup or emergency functional unit intended temporarily to re-establish the function of distribution of gas or vacuum and auxiliary services if the systems within a hospital building or the like should fail in an unforeseen or unwanted manner.

2. Related Art

In a hospital environment, for example in operating theatres, emergency rooms, resuscitation rooms or on the wards, the importance of the availability of medical fluids (oxygen, air, vacuum, etc.) for medium-term and long-term programmed use and for emergency interventions is well known.

It is also known that, for this very reason, appropriate distribution installations are provided, these being structured and equipped in such a way as to make these medical fluids available at several respective "wall outlets" or end-use units installed in a rational manner at locations where they are to be used, for example, in treatment rooms or wards.

These outlets or end-use units arranged on the walls or on fixed or mobile hangers are usually in the form of "nozzles" or connection outlets that can be connected using special connectors and flexible pipes to the medical equipment that uses the medical fluids, for example oxygen masks, devices assisting with breathing or ventilation, devices for aspirating bodily fluids and similar equipment.

It is further known that the regular distribution of medical fluids may suffer from accidental and unforeseeable interruptions, for example caused by damage to the fluid supply pipes, to the components that control, regulate, and interrupt the flow of the various gases involved.

In an attempt to confront these emergency situations, in addition to adopting "backed-up" distribution systems as stipulated in the relevant standards, it is common practice to build up reserves of medical gas which are structurally and functionally independent of the distribution installations, generally loading them into gas cylinders fitted with appropriate components for distributing and controlling the gas.

However, the use of gas cylinders or carboys has numerous disadvantages associated above all with handling them and with the possibility that they may be subjected to accidental impacts, such as droppage, with the risk that the distribution and control components with which they are fitted may become broken or deformed and hence reduce their functionality to a greater or lesser extent.

Furthermore, the vast majority of the gas cylinders kept on standby have the shortcoming of being relatively heavy and large in size, making them somewhat inconvenient, even for specialist personnel, to use in an emergency. Indeed it is known that supply failure situations may create panic and cause even the most experienced of operators to work under conditions of stress that may lead to error or injury with the current equipment available.

Furthermore, when the supply of all medical gases is suddenly interrupted, it is necessary to re-establish all the supplies which is a substantial undertaking with a high probability of errors being introduced owing to the fact that each cylinder contains a different gas.

It should also be emphasized that when use is made of standby gas cylinders kept only for occasional use, there is a potential risk that these cylinders will discharge over time and/or that they will not contain enough gas at the very time that they need to be used.

In addition, there is currently no entirely satisfactory solution for overcoming an unwanted interruption in the centralized distribution of vacuum, that is to say for when the vacuum network used to aspirate the internal cavities of patients becomes unserviceable, for example during a surgical operation, with the exception of certain electrical systems which are, however, of limited capability, such as individual electric aspirators.

In light of that, one problem that needs to be solved is therefore that of being able completely, or at least partially, to overcome the aforesaid disadvantages of the prior art by making it possible in a hospital environment to form a substantial reserve of medical gases and auxiliary services that is completely independent of any conventional distribution installation that might be present such that it can be made available quickly at any point in the hospital environment.

Another object of the invention is to propose a particularly reliable solution that can be deployed effectively in emergency situations while avoiding the potential difficulties associated with the sporadic nature of its use.

In addition, another object of the invention is to prevent the medical and/or paramedical staff from having to perform relatively dangerous manual operations on cylinders for which their normal day to day functions do not suitably prepare them.

Furthermore, the solution of the invention needs to be able to immediately inform the operators as to the actual availability of the product, as to the actual pressure level in the standby gas cylinders and in the secondary distribution network.

SUMMARY OF THE INVENTION

One solution according to the present invention relies on a mobile functional backup unit mounted on wheels for supplying medical gas and vacuum, which unit can be moved around immediately and easily and is rendered functional by the operators in the hospital sector if the normal distribution of medical gas is interrupted in an unforeseen manner, to remove or transport patients out of the department and for rapidly preparing areas for treating patients if they have left in a lying-down position.

More specifically, the invention relates to a mobile functional hospital unit for temporarily distributing medical fluids, the unit being fitted with wheels so that the unit can be moved around over the floor, and comprising:

a cabinet comprising a front wall, a rear wall, side walls, a top and a bottom, and the interior of which defines at least one compartment which houses one or more medical gas cylinders and at least one medical vacuum suction pump, and monitoring and control means designed and able to provide a user with at least one item of information relating to a malfunctioning of the unit, and further comprising:

at least one rear outlet for tapping off medical fluid designed and able to be connected to a medical fluid distribution network arranged within a hospital building and associated with the rear wall of the cabinet, at least one side outlet for tapping off medical fluid associated with at least one side wall of the cabinet, and at least one connecting line fluidically connecting at least one gas cylinder (3, 4; 7, 8) to at least one of the rear and side gas tapping outlets in order to supply at least one of the rear (5, 25) and side outlets with gas delivered by at least one gas cylinder.

The functional unit of the invention may, as the case may be, comprise one or more of the following features:

- the rear fluid-tapping outlet or outlets having an internal fluid-passage diameter greater than the diameter of the side fluid-tapping outlet or outlets, so as to allow a passage of a fluid flow rate, i.e. gas or vacuum, that is greater than that which can flow through the side outlet or outlets;
- it comprises at least two cylinders, preferably two pairs of gas cylinders;
- it comprises at least one pair of cylinders containing a first medical gas, preferably oxygen, and at least one second pair of cylinders containing a second medical gas, different from the first medical gas, preferably medical air;
- the two cylinders of a pair of gas cylinders are connected to a common connecting line connecting the two cylinders of the pair of cylinders to at least one of the rear and side gas tapping outlets;
- the two cylinders of a pair of gas cylinders are connected to a common connecting line connecting the two cylinders of the pair of cylinders to at least one rear gas tapping outlet situated on the rear wall of the cabinet and to at least one side gas tapping outlet situated on the side wall of the cabinet;
- a solenoid valve is provided on at least one, or on each connecting line, preferably one or all of the solenoid valves are controlled by the monitoring and control means;
- at least one rear outlet and/or at least one side outlet for tapping off medical fluid is a vacuum suction outlet and at least one rear outlet and/or at least one side outlet for tapping off medical fluid is an outlet for distributing gas, particularly oxygen or medical air;
- on at least one, or on each connecting line there are, in series between the gas cylinder or cylinders and the corresponding connecting outlet or outlets, a pressure regulator, a non-return valve and a solenoid valve, and the solenoid valve is preferably normally open;
- at least one rear outlet and at least one side outlet are vacuum suction outlets fluidically connected, via at least one vacuum line, to the suction intake of the suction pump so that a partial vacuum can be created at the outlets;
- it comprises at least one side connecting outlet and at least one rear connecting outlet for a first type of medical gas, in particular oxygen, and at least one side connecting outlet and at least one rear connecting outlet for a second type of medical gas, in particular medical air;
- the side connecting outlets are duplicated on the two opposite side walls of the cabinet;
- the front wall of the cabinet comprises a control panel, and the control panel preferably comprises a keypad and/or a display collaborating with the monitoring and control means;
- at least one of the side walls has a door providing access to the internal compartment containing the cylinder or cylinders or to the internal compartment containing the pump, and at least one door is preferably provided on each of the side walls.
- it comprises a backup electric battery designed to be able to supply the monitoring and control means and/or the solenoid valve or valves with electrical current particularly if the mains supply should fail;
- it comprises handles formed on one or more of the side, front or rear walls;
- the top of the cabinet forms a dish in which objects can be placed;
- the interior of the cabinet comprises at least one main compartment housing one or more medical gas cylinders and at least one additional compartment in which at least the suction pump is positioned, the compartments each being fitted with one or more access doors and the additional compartment is preferably closed by a door that has ventilation slots;
- at least one rear outlet for tapping off medical gas fluid is positioned at the upper end of the rear wall and near the top and/or at least one side outlet for tapping off medical fluid is positioned at the upper end of at least one side wall and near the top;
- at least an upper part of the front face is inclined with respect to a vertical plane, the inclined upper part of the front wall bearing the control panel;
- the monitoring and control means are designed and able to transmit alarm signals in order to alert the user to any malfunctioning of the unit, the malfunctioning being chosen among a reduction in the quantity or pressure of gas in one of the cylinders below a fixed threshold value; an increase in the temperature of the pump valve above a given maximum temperature value; detection that at least one door is open; defective operation of at least one valve or sensor positioned on the vacuum line or on the connecting line; a reduction in the vacuum pressure below a fixed threshold value; a battery charge below a fixed threshold value; or the fact that the unit is overdue a service;
- the monitoring and control means are designed and able to transmit audible and/or visible alarm signals to alert the user to any malfunctioning and/or to display information about the malfunction on the display screen;
- if a malfunction is detected, the monitoring and control means are designed and able to act on the pump in such a way as to stop it from running, to act on a solenoid valve positioned on the outlet side of the cylinders in order to close this valve, or to allow the gas to pass into the connecting line.

BRIEF DESCRIPTION OF THE FIGURES

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

The figures show a functional emergency unit 1 according to the present invention intended to provide an emergency supply of medical gases to the distribution installation situated, such as, for example, in a hospital environment. The unit 1 according to the present invention is of the type which comprises at least one backup cylinder of medical gas, such as, for example of oxygen, of medical air, of a He/O$_2$ mixture, of a N$_2$O/O$_2$ mixture or any other medical gas.

The unit 1 comprises a cabinet 2 which houses at least one pair of medical gas cylinders 3, 4, at least one gas tapping outlet 5 which may be fixed to the quick coupling of the gas tapping pipes and associated with a rear wall 6 of the cabinet 2, a flow coupling 9 between each cylinder 3, 4 of the at least one pair of cylinders and the connecting outlet 5, and a trolley or bottom 10 supporting the cabinet 2.

The trolley 10 is mounted on wheels 12 fixed such that they can pivot and provided with a locking device making the unit 1 easy to move around in hospital or similar areas, with a great degree of freedom while at the same time allowing it to be kept in a stable position when it is in use. Furthermore, the corners of the trolley 10 are fitted with corner buffers 13 which protect either the unit 1 or individuals or items situated in its vicinity while it is being moved around and immobilized.

The cabinet 2 is preferably of compact dimensions, namely of a height of between 100 and 150 cm, for example of about 144 cm; a width of between about 50 and 90 cm, for example of about 71 cm; and a depth of between about 70 and 110 cm, for example of about 89 cm. The particularly compact dimensions and the extreme ease of movement on wheels 12 make the unit extremely convenient for operators in the hospital sector to use in an emergency or even non-routine situation.

The cabinet also comprises a front wall 16 on which there is a control panel 40, a rear wall 6 and two side walls 27, 28. Most of the upper part of the front wall 16 on which the control panel 40 is housed is inclined to make the control panel 40 easier for the operator to see and to read.

A tray 33 in which objects can be placed is recessed into the top of the cabinet 2 and can be used to house various items or care equipment or the like.

Furthermore, two handles, for example of the bar type 32, are positioned on each of the side walls 27, 28. A handle is also provided on the rear part 6. The handles 32 allow the emergency apparatus to be attached using appropriate clamps. They can also be used as something to grasp in order to move the unit 1 over the ground.

The interior of the cabinet 2 defines at least one pair of compartments 29 which may or may not be symmetric, just one of which has been depicted in the figures and in each of which is housed a pair of selected medical gas cylinders 3, 4 whereas, for each pair of cylinders 3, 4, one or more respective gas tapping outlets 21, 22, 23, 24 are provided at least on one of the side walls 27, 28 of the cabinet 2 so that they can be connected to the quick coupling of gas tapping accessories such as ventilators to assist with breathing or the like.

More specifically, the functional unit 1 comprises at least one pair of cylinders 3, 4, for a first type of medical gas, for example oxygen, and at least one second pair of cylinders 7, 8 for a second type of medical gas, for example air of medical quality.

In another embodiment, another compartment 29' accessible via a front door 34 or side door 39' is formed in the cabinet 2 and houses a suction pump 18 a suction nozzle of which communicates with a vacuum wall outlet 17 associated with at least one of the side walls 27, 28 of the cabinet 2. As a preference, the gas cylinders, arranged in pairs 3, 4 or 7, 8 have a capacity of about 14 liters for example and a diameter of 171 mm with a height of 920 mm. The two cylinders 3, 4 for oxygen and 7, 8 for medical air are preferably equipped with automatic switching control: the normally-open solenoid valve 11 is operated by the control means 35.

Figure 4:
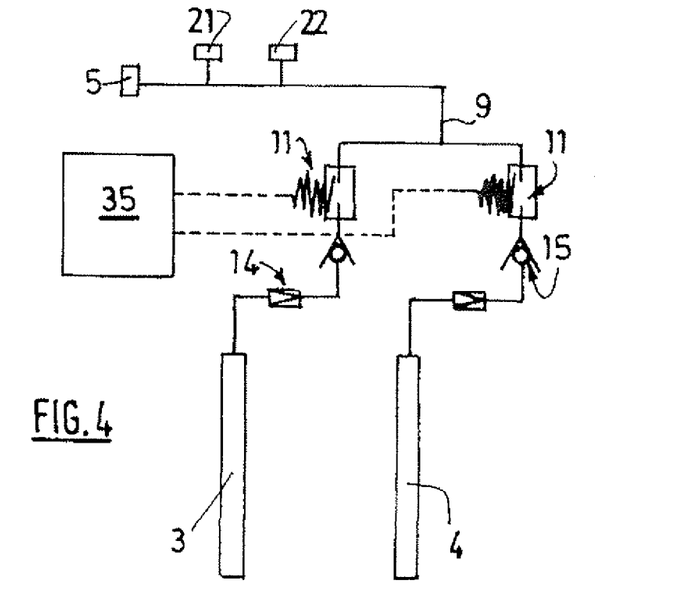
FIG. 4 is a schematic block diagram of the components that form part of the unit of FIG. 1.

As can be seen in FIG. 4, two solenoid valves 11 are advantageously provided on the flow coupling 9 between each cylinder 3, 4 or 7, 8 of each pair of cylinders and the corresponding connection outlet 5.

Even more specifically, on each flow coupling 9 provided between each cylinder of a pair of cylinders 3, 4 or 7, 8 and the corresponding connecting outlet 5 there are, in series: a pressure reducer 14 provided with a manometer and with a pressure regulator transducer, a nonreturn valve 15 and a solenoid valve 11 which is normally open and is operated via the monitoring and control means 35.

Figure 1:
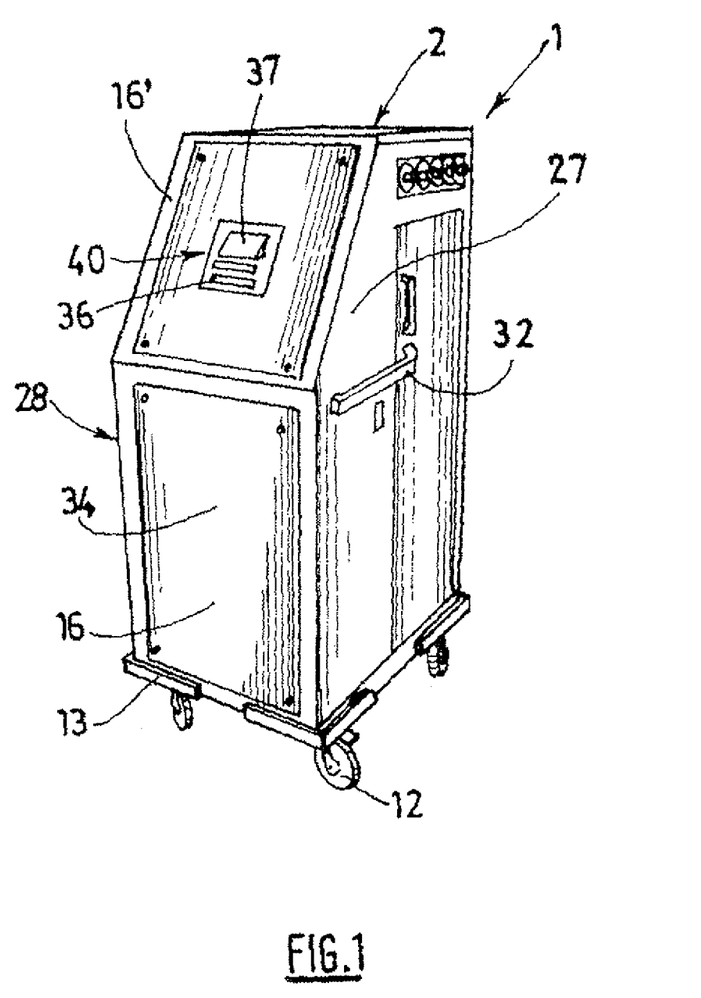
FIG. 1 depicts a view in perspective and in vertical elevation of the backup or emergency unit according to the present invention.
Figure 2:
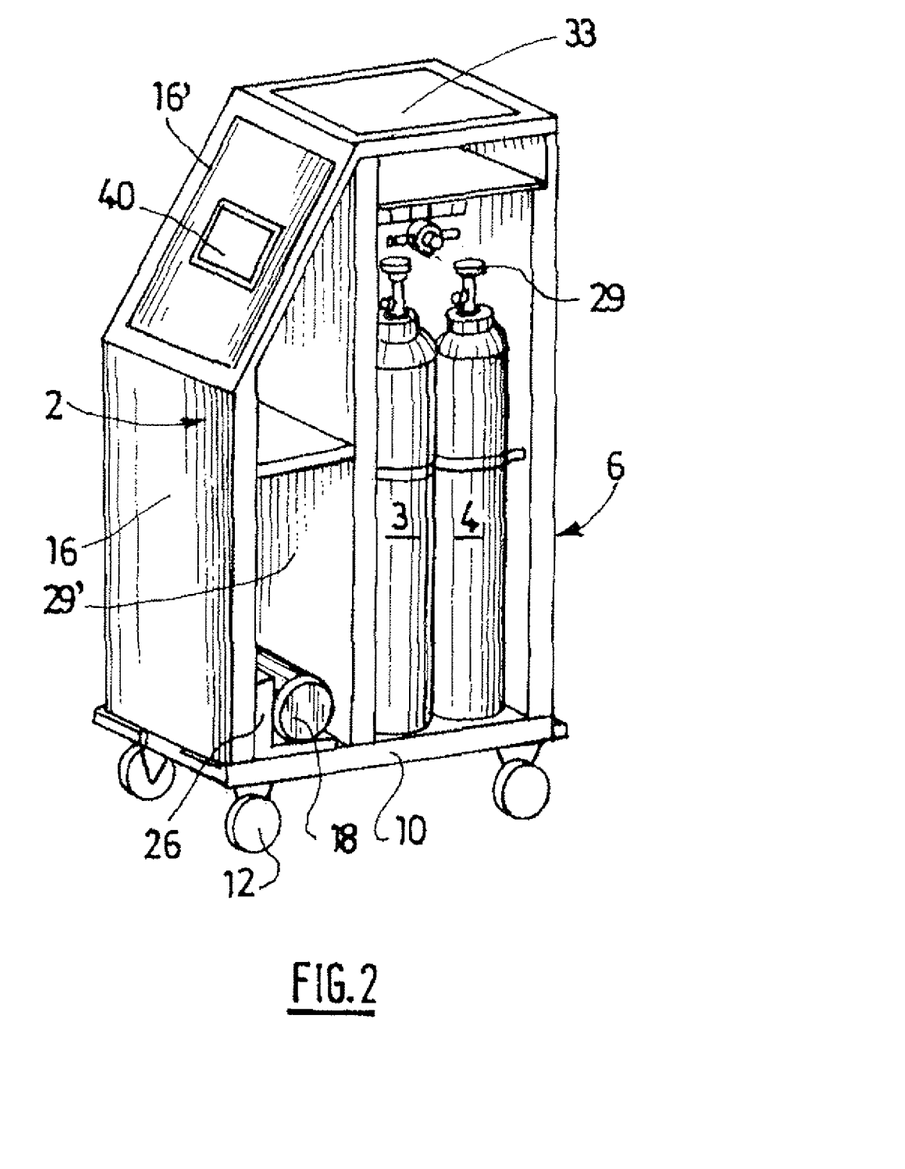
FIG. 2 depicts a schematic perspective view of the unit of FIG. 1, partially open.
Figure 3:
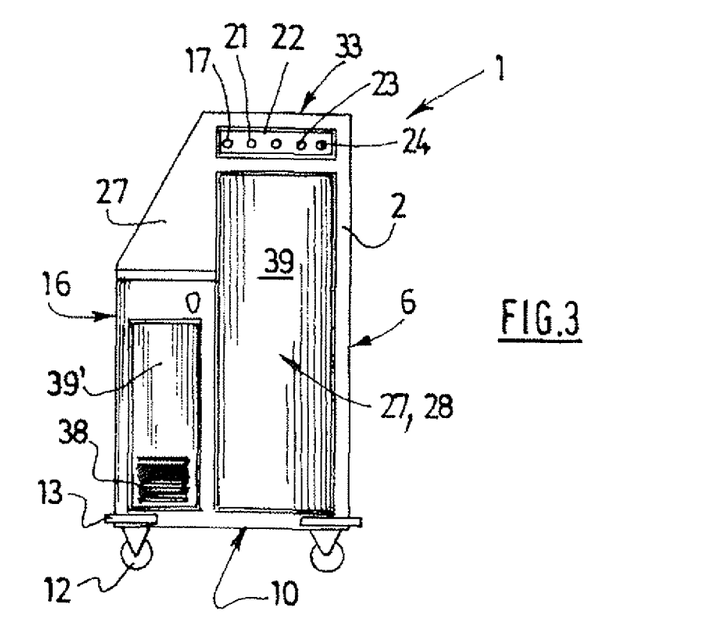
FIG. 3 depicts a schematic side view of the unit according to the invention.
Figure 5:
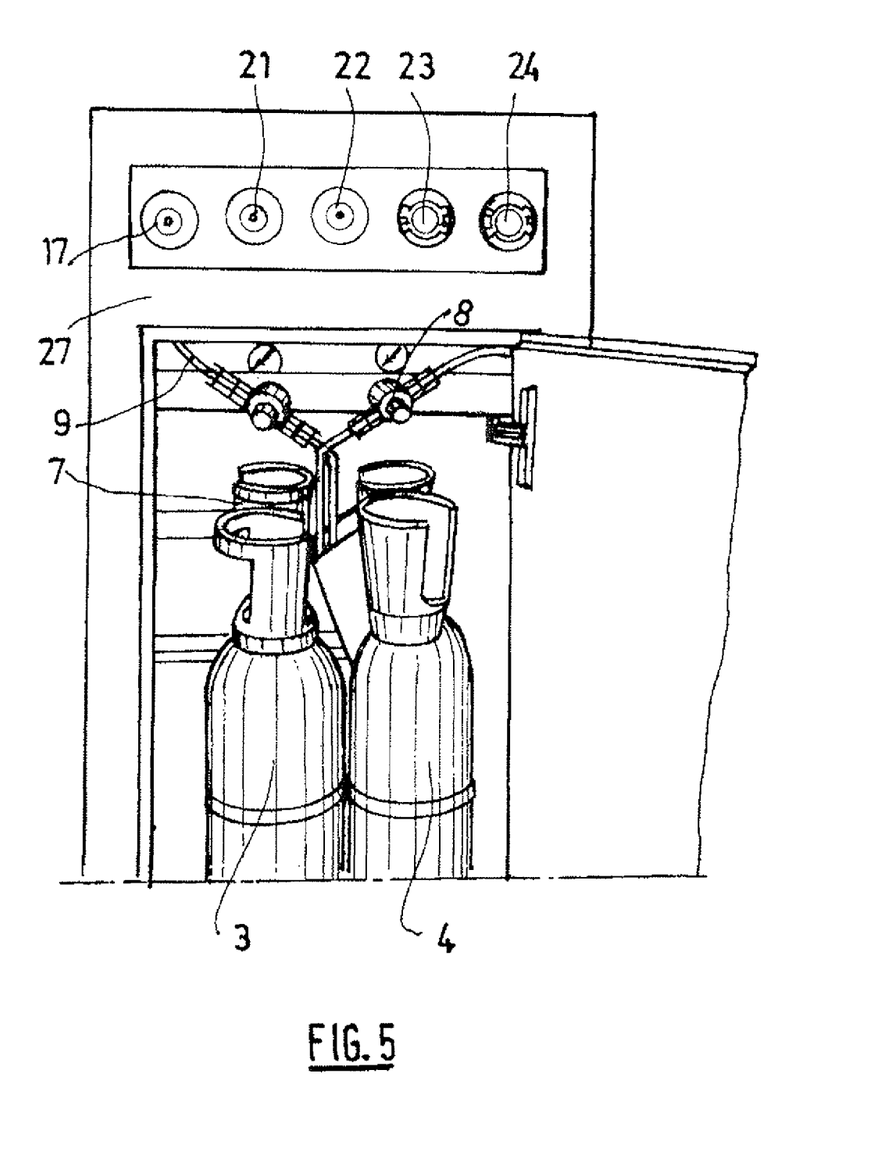
FIG. 5 depicts a schematic side view of a detail of the functional unit according to the present invention.

As schematically depicted in FIGS. 1, 3 and 5, the unit 1 here comprises five gas tapping outlets, namely one outlet 17 for a vacuum, two oxygen outlets 21, 22 and two outlets 23, 24, for compressed air at 400 kPa, which outlets are formed near the top of each side wall 27, 28 of the cabinet 2.

These outlets are preferably of a standardized type, for example of the AFNOR NF-S 90-116 or UNI 9507 type. The type plates for the oxygen outlets 21, 22 are white in color, whereas those for the compressed air outlets 23, 24 are distinguishable by an alternation of black and white circular sectors so that they can be identified more easily and more immediately and in accordance with the relevant standards. The type plate for the vacuum outlet 17 is yellow in color so that it too can be readily discerned.

Figure 6:
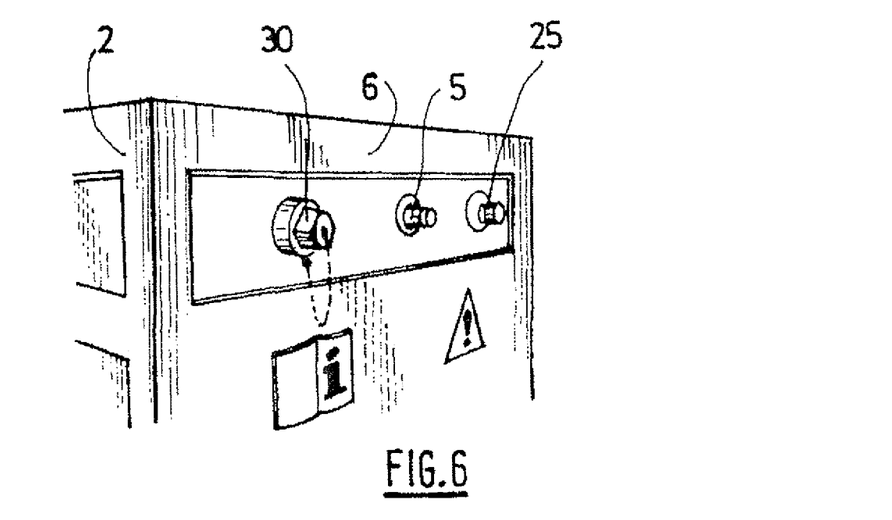
FIG. 6 depicts a perspective view of another detail of the rear of the functional unit according to the present invention.

Furthermore, additional gas tapping outlets 5, 25 and 30 for oxygen, compressed air, and vacuum respectively are advantageously provided near the top of the rear wall 6 of the cabinet 2. These outlets can be quickly and easily connected to the internal pipework network at the hospital or the like. The additional outlets 5, 25 are of the NIST EN 739 type for medical gases, while the vacuum outlet 30 is essentially formed of a threaded coupling with a gasket made in three parts, for example with a diameter of 19 mm. The colors of the type plates correspond to those of the other outlets provided on the side walls.

Unlike the outlets present on the side walls 27 and 28 which are designed to allow medical gases to be tapped using flexible couplings connected to the apparatus and operated directly by the healthcare personnel using the unit 1, these other additional outlets 5, 25 and 30 are specifically designed and able to be connected to the emergency inlets of the reduction panels of the medical gas low-pressure distribution network of the hospital building in the event of an emergency caused by the unforeseen loss of or drop in the fixed supply from the network arranged in the hospital or similar building.

By virtue of the additional outlets 5, 25 or 30 the functional unit 1 genuinely and intrinsically becomes an emergency unit intended to be used in the event of unforeseen failure of the medical gas distribution main supply in hospital departments in order to guarantee continuity of distribution through the wall outlets situated in departments relatively remote from the unit 1.

All the outlets present on the side walls 27, 28 and on the rear wall 6 of the cabinet 2 are connected to the flow for the respective gas cylinders or to the suction pump 18 by flow couplings on which the shut-off means 14, 15, and 11 already described are fitted. The cylinders 3, 4 or 7, 8 have their own shut-off valve. An antibacteriological filter is positioned just before the pump to "eliminate" dirt, bacteria, etc. (this is not shown).

As shown in FIG. 4, it should be noted that each backup cylinder 3, 4 or 7, 8 is associated with a pressure regulator 14 and with a stop valve 15 so that the flow of gas can be shut off when the cylinder is being replaced.

A normally-open solenoid valve 11 controlled by monitoring and control means 35, particularly a central electronic unit which will be described later on, is inserted in the flow line 9 downstream of the valve 15.

The solenoid valve 11 allows the flow of gas from one of the cylinders to be stopped automatically and switched over to the fluid from the other cylinder. This is done by operating the solenoid valve 11 via the monitoring and control means 35.

The flow line 9 simultaneously feeds the outlets installed on the side walls 27, 28 and on the rear wall 6. These are, more specifically, oxygen outlets 21, 22 provided on the side walls 27, corresponding outlets provided on the wall 28 and the outlet 5 provided on the rear wall 6. Similarly, in the case of medical air, these are the outlets 23, 24 provided on the side wall 27, corresponding outlets provided on the wall 28 and the outlet 25 provided on the rear wall 6. The outlets can be connected to a corresponding external coupling only one after the other.

In all events, at least one outlet 5 for tapping off medical gas fluids is associated with the rear wall 6 of the cabinet 2 and is specifically designed to ensure the continuity of medical fluid supply by the centralized medical gas distribution installation in the event of an emergency brought about by the unforeseen loss of or drop in the fixed supply from the centralized distribution installation in the knowledge that, in the case of medical gases, the current standards demand that emergency outlets to which the functional unit 1 can be connected be kept available on second-line units.

Furthermore, at least one gas tapping outlet 23 is associated with at least one side wall 27, 28 of the cabinet 2 and is designed to allow the medical gases to be tapped off using flexible couplings connected to the apparatus for medical devices actuated directly by the healthcare personnel using the unit 1.

For aspiration, the vacuum outlet 30 is connected, using flexible couplings, to another new medical device installed on the centralized distribution installation, namely a wall-mounted shut-off valve for medical aspiration with emergency inlet.

Furthermore, the functional unit 1 advantageously comprises control means, namely an electronic control unit 35 arranged in a compartment situated under the control panel 40. The monitoring and control means 35, also known as the electronic control unit 35, comprise a power supply module, an evaluation and operating module and an actual control module, the latter containing power components which drive each of the electronic or electromechanical actuators of the unit 1, for example the various solenoid valves 11 or the pump 18.

The power supply module of the electronic control unit 35 is designed to regulate the electronic power supply of the electronic control unit 35 and of the entire unit 1. For example, a conventional mains power supply of 235 V AC+/−10%, 50-60 Hz, with a double pole outlet and earth switch and fuse box, and a backup or standby power supply using electric batteries carried on board the unit 1 and accessible via the front door 34 is provided here.

More generally, the electronic control unit 35 has the role of providing an electrical power supply to all the electrical components of the unit 1 if the mains power supply should fail.

The evaluation and operating part of the electronic control unit 35 comprises a microprocessor unit and conventional read-only or read-write memories that enable this electronic control unit to operate correctly.

Signals originating from detectors or sensors detecting or sensing pressure, temperature and/or on/off status associated with the cylinders 3, 4, 7, 8 and with the suction pump 18, with the housing in which it is located and with the panels providing access to the housings are sent to the electronic control unit 35. The other operating signals reach the electronic control unit 35 via a keypad 36 available to the operators and situated on the control panel 40.

As will be seen hereinafter with reference to FIG. 7, by processing the input signals the electronic control unit 35 is able to display on a backlit liquid crystal display (LCD) 37 of the control panel 40 precise information regarding the operating status of the unit 1 and regarding the amount and pressure of the gases present in the cylinders held within this unit 1.

As has already been stated, the installation for pulling and creating a vacuum provided inside the compartment 29 of the cabinet 2 comprises the vacuum pump 18, for example a Rietschle VCB20 model with a suction capacity of 20 m$^3$/h. Ventilation or a fan of the 26 to 24 V type for performing heat exchange in the compartment 29 and intended to run at the same time as the pump 18, and a thermostatic probe for monitoring the operating temperature of the pump 18 are also provided.

The probe is connected to the control means 35. That being the case, when it nears the limit of a first safety temperature (+50° C.), the pump 18 is switched off and the ventilation system 26 continues to operate until the compartment 29 has dropped back below a second safety temperature (+40° C.). In this case, the pump 18 will have to be restarted by hand for forced operation.

The electronic control unit 35 advantageously instigates a programmed running of the pump 18, for example every 15 days, while the module 2 is stably connected to the mains and is on standby with the machine not running. This activation may for example last for a preset length of time (120 seconds), with a corresponding display on the screen 37, for example "vacuum pump check: do not touch any key in the next 120 s, a functional test is about to be run".

During this period devoted to the test, the unit 1 cannot be used. For the test period, use of the trolley 10 takes priority.

Figure 7:
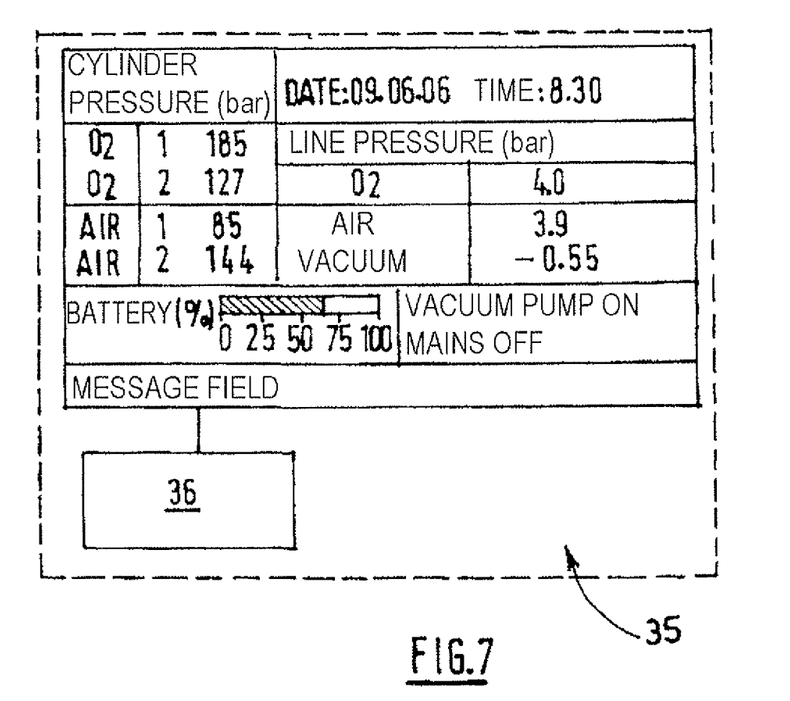
FIG. 7 depicts a schematic view of an electronic control unit associated with a screen and with a keypad that forms the interface with the users of the functional unit according to the present invention.

With reference to FIG. 7, the electronic control unit 35 manages all the functions of the unit 1 through the keypad 36 and the display 37, for example as follows:

- the possibility of presenting information in various languages,
- signals that a connector is present by emitting an audible alarm,
- displaying the logo and the name of the product or of the company for a preset brief duration,
- access to a help function, to manufacturing and installation data, output, indicates the pressure in the cylinders (checked using the pressure transducer located on the high-pressure side of the regulator 14), refreshes the numerical values every 5 seconds for example, manages the switching between the cylinders supplying the oxygen circuit and the 400 kPa compressed air circuit, alarm status (indicates by the lighting of a red LED under the key that has been moved), cylinder maintenance thresholds: 130 bar—successive indication every 30 bar with an audible alarm lasting 3 s—switching of the cylinder at 10 bar with a continuous audible alarm that can be cancelled—specific error message if the cylinder is exhausted and/or absent, low line-pressure alarm (3.2 bar), may be interrupted; the cancellation time can be set by the user up to a maximum of 15 minutes, high line-pressure alarm (4.8 bar) which can be interrupted with an adjustable cancellation period, low partial-vacuum alarm (−0.6 bar) which can be interrupted with an adjustable cancellation period.

It should be noted that when a partial vacuum value of below −0.2 is reached for longer than 180 s, the pump is switched off and will have to be restarted by hand.

In other words, software built into the control means 35 provides management and control of the alarms and of the effectiveness of the functional unit 1. This software is embedded in the electronic control unit 35 which receives the commands from the keypad 36 formed on the cabinet 2 and has other signal inputs connected to pressure detectors associated with each cylinder 3, 4, the electronic control unit 35 being connected to a display 37 situated on the cabinet and having control outputs for the actuators 11 that shut off the fluid situated on the coupling or couplings or flow line 9 and in respect of the suction pump 18.

The electronic control unit 35 is characterized by its ability, via the display 37 (cf. FIG. 7), to inform the medical operator as to the operating status of the emergency unit, as to the remaining pressure in the cylinders, as to the flow rates at which the medical gases are being distributed and as to the remaining time for which gases contained in the pairs of cylinders 3, 4 or 7, 8 for the highest output flow rates will be available.

This software also, for one and the same gas, automatically switches from the "empty" (pressure at 10 bar) first cylinder to the full second cylinder. It should be noted that a shut off valve may be fitted on the vacuum pipe. Continuing to list other functions offered to the operator of the unit 1, it should be pointed out that the following information is available to the user:

an alarm that the service doors (right, left, central) are open, only the alarm associated with the central door will stop the vacuum pump 18, electronic or software error with communication of the error code, temperature limits for the valve connected to the pump (+40° C./+50° C.) with thereafter a command to lock down the pump 18, routine service (pump, filter, end units) almost due, this being flagged up from the thirtieth day before the service is due, all the alarms can be seen on the relevant line of the main screen, with a sequence of at least three seconds for each alarm and priority accorded to the essential functions. By pressing a pushbutton (arrow downwards) it is possible to switch to another screen devoted to displaying alarms.

After a period of inactivity lasting about 1 minute, the unit automatically switches to a main menu screen. Furthermore, it also provides the following information:

the various line pressures and partial vacuums, the level of charge in the backup battery, whether it is mains powered, whether the vacuum pump is operating, the date and the time, the number of liters actually present in the cylinders, indicating the instantaneous consumption as calculated from the reduction in pressure in the cylinder every three minutes for each gas and the residual autonomy in the most critical situations (acquired at 10+10 bar of pressure for switching over each cylinder), alarm log management with information on the appropriate screen (the last thirty significant alarms) and downloading of files via an RS 485 outlet together with the printing of the logs and/or of the handling activities performed (machine status), menu for the handling part with an indication of which parts require servicing, accessible using the maintenance booklet, through use of a password for several operators, the need to replace the filter (run time returned to zero) every x hours of operation and/or every twelve months, need to replace the pump oil (run time set to zero) every x hours of operation and every twelve months, need to replace the pump separating filter (run time set to zero) every x hours of operation and every twelve months, need to replace the outlet maintenance kit (run time set to zero) every twelve months, periodic check of the cabinet 2 according to an operating schedule and at regular intervals.

From the foregoing description it is clearly evident that the functional unit according to the invention is able to remedy the difficulties of the prior art and to afford other advantages namely, in particular:

the particularly compact dimensions and the extreme ease of movement on wheels makes the unit 1 extremely convenient for operators in the hospital sector to use, whether this be in an emergency situation or during non-routine operations;

the side walls of the cabinet 2 are essentially smooth, which amounts to saying that they are hygienic and able to prevent accidents;

furthermore the perfectly flat top tray is removable so that working implements can be placed therein;

given the limited dimensions, its footprint is minimal and, in any event, no space is lost because the unit offers a useful support area at the typical height of a work surface.

In practice, the unit is of vital importance to patients and operators in the sector who have to use it in an emergency situation. To this end, the trolley is in particular equipped with wheels 12 mounted such that they can pivot and its corners have corner pads 13 to make it even safer to use.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A mobile functional hospital unit for temporarily distributing medical fluids, the unit being fitted with wheels so that the unit can be moved around over the floor and comprising:
   a cabinet comprising a front wall, a rear wall, side walls, a top, and a bottom, the interior of the cabinet which defines at least one compartment which houses one or more medical gas cylinders and at least one medical vacuum suction pump;
   the wheels of the unit being such that one wheel corresponds to each corner of the bottom of the unit with each wheel being pivotally mounted and including a locking device;
   monitoring and control means designed and able to provide a user with at least one item of information relating to a malfunctioning of the unit,
   at least one rear outlet for tapping off medical fluid designed and able to be connected to a medical fluid distribution network arranged within a hospital building and associated with the rear wall of the cabinet;
   at least one side outlet for tapping off medical fluid associated with at least one of the side walls of the cabinet; and
   at least one connecting line fluidically connecting at least one gas cylinder to at least one of the rear and side gas tapping outlets in order to supply at least one of the rear and side outlets with gas delivered by at least one gas cylinder.

2. The unit of claim 1, wherein the unit comprises at least two cylinders.

3. The unit of claim 2, wherein the unit comprises at least one pair of cylinders containing a first medical gas and at least one second pair of cylinders containing a second medical gas.

4. The unit of claim 3, wherein the first medical gas is oxygen.

5. The unit of claim 3, wherein the second medical gas is air.

6. The unit of claim 4, wherein the second medical gas is air.

7. The unit of claim 1, wherein the at least one rear fluid-tapping outlet has an internal fluid-passage diameter greater than the diameter of the at least one side fluid-tapping outlet.

8. The unit of claim 3, wherein the two cylinders of a pair of gas cylinders are connected to a common connecting line connecting the two cylinders of the pair of cylinders to at least one of the rear and side gas tapping outlets.

9. The unit of claim 3, wherein the two cylinders of a pair of gas cylinders are connected to a common connecting line connecting the two cylinders of the pair of cylinders to at least one rear gas tapping outlet situated on the rear wall of the cabinet and to at least one side gas tapping outlet situated on the side wall of the cabinet.

10. The unit of claim 1, wherein a solenoid valve is provided on each connecting line.

11. The unit of claim 1, wherein a solenoid valve is provided on at least one connecting line.

12. The unit of claim 1, wherein at least one rear outlet and/or at least one side outlet for tapping off medical fluid is a vacuum suction outlet and at least one rear outlet and/or at least one side outlet for tapping off medical fluid is an outlet for distributing gas.

13. The unit of claim 1, wherein on each connecting line there are, in series between the gas cylinder or cylinders and the corresponding connecting outlet or outlets, a pressure regulator, a non-return valve and a solenoid valve.

14. The unit of claim 1, wherein on at least one connecting line there are, in series between the gas cylinder or cylinders and the corresponding connecting outlet or outlets, a pressure regulator, a non-return valve and a solenoid valve.

15. The unit of claim 1, wherein at least one rear outlet and at least one side outlet are vacuum suction outlets fluidically connected, via at least one vacuum line, to the suction intake of the suction pump so that a partial vacuum can be created at the outlets.

16. The unit of claim 1, wherein the unit comprises at least one side connecting outlet and at least one rear connecting outlet for a first type of medical gas and at least one side connecting outlet and at least one rear connecting outlet for a second type of medical gas.

17. The unit of claim 1, wherein the side connecting outlets are duplicated on the two opposite side walls of the cabinet.

18. The unit of claim 1, wherein the front wall of the cabinet comprises a control panel.

19. The unit of claim 1, wherein the control panel comprises a keypad and/or a display collaborating with the monitoring and control means.

20. The unit of claim 1, wherein at least one of the side walls has a door providing access to the internal compartment containing the cylinder or cylinders or to the internal compartment containing the pump.

21. The unit of claim 20, wherein at least one door is preferably provided on each of the side walls.

22. The unit of claim 1, wherein the interior of the cabinet comprises at least one main compartment housing one or more medical gas cylinders and at least one additional compartment in which at least the suction pump is positioned, the compartments each being fitted with one or more access doors.

23. The unit of claim 22, wherein the additional compartment is closed by a door that has ventilation slots.

24. The unit of claim 1, wherein at least one rear outlet for tapping off medical gas fluid is positioned at the upper end of the rear wall and near the top and/or at least one side outlet for tapping off medical fluid is positioned at the upper end of at least one side wall and near the top.

25. The unit of claim 1, wherein at least an upper part of the front face is inclined with respect to a vertical plane, the inclined upper part of the front wall bearing the control panel.

26. The unit of claim 1, wherein the monitoring and control means are designed and able to transmit alarm signals in order to alert the user to any malfunctioning of the unit, the malfunctioning being chosen among a reduction in the quantity or pressure of gas in one of the cylinders below a fixed threshold value; an increase in the temperature of the pump valve above a given maximum temperature value; detection that at least one door is open; defective operation of at least one valve or sensor positioned on the vacuum line or on the connecting line; a reduction in the vacuum pressure below a fixed threshold value; a battery charge below a fixed threshold value; or the fact that the unit is overdue for service.

27. The unit of claim 1, wherein the monitoring and control means are designed and able to transmit audible and/or visible alarm signals to alert the user to any malfunctioning and/or to display information about the malfunction on the display screen.

28. The unit of claim 1, wherein if a malfunction is detected, the monitoring and control means are designed and able to act on the pump in such a way as to stop it running, to act on a solenoid valve positioned on the outlet side of the cylinders in order to close this valve, or to allow the gas to pass into the connecting line.

* * * * *